United States Patent [19]

Chung

[11] 4,328,160

[45] May 4, 1982

[54] PROCESS FOR THE PREPARATION OF 1-AMINOANTHRAQUINONES

[75] Inventor: Rack H. Chung, Clifton Park, N.Y.

[73] Assignee: BASF Wyandotte Corporation, Wyandotte, Mich.

[21] Appl. No.: 834,992

[22] Filed: Sep. 20, 1977

[51] Int. Cl.$^3$ .................. C07C 97/24; C07C 97/26; C07C 143/665
[52] U.S. Cl. ..................... 260/378; 260/384; 260/371; 260/373; 260/380; 260/381
[58] Field of Search ............... 260/369, 384, 376, 522, 260/378, 371, 373, 380, 381

[56] References Cited

U.S. PATENT DOCUMENTS

| | | | |
|---|---|---|---|
| 1,551,373 | 8/1925 | Daudt | 260/522 |
| 1,966,067 | 7/1934 | Jaeger | 260/522 |
| 2,439,237 | 4/1948 | Cass | 260/522 |
| 3,978,096 | 8/1976 | Eilingsfeld et al. | 260/384 |

FOREIGN PATENT DOCUMENTS 678608  9/1952  United Kingdom ............... 260/376

OTHER PUBLICATIONS

*Methoden der Organischen Chemie*, Houben–Weyl, vol. 8, pp. 484–496.
*Journal of the Society of Dyers & Colorists*, vol. 66, pp. 229–231, Apr. 1950, "Aromatic Nitro Compounds", Hodgson, Heyworth & Ward.
*Chemical Abstracts*, vol. 71, 1969, Abstract No. 48900m, Long "Mechanisms for Decarboxylation of Aromatic Acids".
*Chemical Abstracts* vol. 74, 1974, Abstract No. 52664s, p. 268, Manikyam "Thermal Decarboxylation of Benzoic Acids".
*Chemical Abstracts* vol. 74, 1971, Abstract No. 64020s, p. 287, Chodowska-Palicka "Decarboxylation of 2 Nitro Benzoic Acids".
*Chemical Abstracts*, vol. 67, 1967 Abstract No. 43191p, p. 4036, Rekker et al. "Decarboxylation of Substituted 4-Amino Benzoic Acid in Aqueous Solution".
*Chemical Abstracts*, vol. 85, 1976, Abstract No. 177120v, p. 495, Morley, "Synthesis of Aminoanthraquinones by Sodium Borohydride Reduction of Nitroanthraquiones".

*Primary Examiner*—Winston A. Douglas
*Assistant Examiner*—Raymond Covington
*Attorney, Agent, or Firm*—Joseph D. Michaels; Samson B. Leavitt

[57] ABSTRACT

A selective process for the preparation of 1-aminoanthraquinones from the corresponding 1-aminoanthraquinone-2-carboxylic acid by decarboxylation in basic solution in the presence of iron, tin or zinc as a catalyst.

10 Claims, No Drawings

PROCESS FOR THE PREPARATION OF 1-AMINOANTHRAQUINONES

The present invention provides a simplified and efficient process for selectively producing 1-aminoanthraquinones in a substantially pure state and in high yield.

The 1-aminoanthraquinone is an important intermediate in the manufacture of a wide variety of dyestuffs, pharmaceuticals, thickening agents, etc., being used either as such or after conversion to a corresponding derivative. Specifically, 1-aminoanthraquinone is used in the manufacture of bromamine acid and 1-amino-2-bromo-4-hydroxyanthraquinone from which Genacron Cerise N and Genacron Cerise NSL and other valuable dyestuffs are produced.

Typical reactions for the 1-aminoanthraquinone isomer are treatment with concentrated oleum or chlorosulfonic acid to form the 1-amino-2-sulfonic acid derivative followed by treatment with bromine to form bromamine (1-amino-4-bromoanthraquinone-2-sulfonic acid), or the 1-aminoanthraquinone compound can be dibrominated to form 2,4-dibromo-1aminoanthraquinone, which, in turn can be hydrolyzed with concentrated sulfuric and boric acids to provide 1-amino-2-bromo-4-hydroxyanthraquinone. The 1-aminoanthraquinone can also be treated with chlorofom to give the isocyanide derivative and reaction with nitrous acid gives the corresponding diazonium salt which, in turn, is hydrolyzed to the hydroxy derivative.

In the past, 1-aminoanthraquinone has been prepared by treatment of anthraquinone with oleum in the presence of mercury to produce anthaquinone-1-sulfonic acid which, in turn, is reacted with ammonia in the presence of arsenic. Since the present process does not require mercury or arsenic, it avoids serious pollution problems associated with their use and disposal.

Further disadvantages of prior processes using mercury and arsenic appear to be due to the fact that traces of these elements can be found in the final product, which are prohibitive in the preparation of pharmaceuticals.

Accordingly, it is an object of the present invention to provide a commercially feasible and economical process for the selective production of 1-aminoanthraquinone and substituted derivatives thereof.

It is another object of the present invention to provide a process for the production of 1-aminoanthraquinone in high yield and in a substantially pure state, e.g. above about 95%.

These and other objects of the present invention will become apparent from the following description and disclosure.

In accordance with the present invention, a 1-aminoanthraquinone-2-carboxylic acid having the formula:

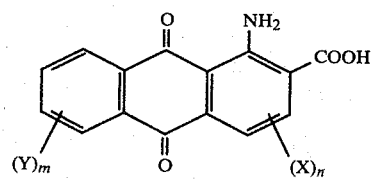

wherein X is hydroxy, alkoxy of from 1 to 4 carbon atoms, halo, amino or —SO$_3$H; Y is hydroxy, alkoxy of from 1 to 4 atoms, halo, amino or —SO$_3$H; and m and n independently represent a value of from 0 to 2, is dissolved in an alkali metal hydroxide solution or ammonium hydroxide solution and decarboxylated in the presence of iron, tin or zinc in particulate form, at a temperature of from about 50° C. to about 150° C. under from about 5 to about 100 psig, preferably at a temperature of from about 80° C. to about 110° C. or reflux under atmospheric pressure.

The alkaline solution of 11-aminoanthraquinone-2-carboxylic acid is preferably prepared by dissolving the acid in an aqueous solution of an alkali metal hydroxide, preferably KOH, NaOH or NH$_4$OH, of between about 0.1 molar and about 5 molar concentration, preferably between about 1.00 molar and about 3.0 molar concentration. The moles of alkali metal hydroxide per mole of acid may vary between about 2 and about 20, and is preferably between about 3 and about 15. To this solution is added from about 0.1 mole to about 0.5 moles, more desirably between about 0.2 moles and about 0.4 moles, of the metal catalyst per mole of 1-aminoanthraquinone-2-carboxylic acid. The mixture is then reacted at elevated temperature, preferably by refluxing for a period of from about 0.5 to about 8 hours, more desirably from about 0.5 to about 4 hours, during which time carbon dioxide gas is generated. The carbon dioxide by-product can be vented to the atmosphere or the reaction can be conducted in a closed system wherein the generation of carbon dioxide gradually increases the pressure and the reaction is run under autogenous conditions. If desired, the reaction can be run under a blanket of nitrogen gas; although such operation under nitrogen is not necessary to achieve the benefits of the present invention. A pH of between about 8 and about 10 is maintained during reaction.

After the reaction is completed as noted by constant pressure or cessation of carbon dioxide generation, the reaction product which is formed as a precipitate, is cooled, filtered, and freed of metal catalyst by heating to between about 80° C. and about 120° C., preferably between about 90° C. and about 100° C., with 30–60% aqueous solution of a mineral acid such as H$_2$SO$_4$ or HCl and then diluting the resulting mixture with from about 0.5 to about 5 volumes of water. In this reaction the metal is converted to a salt which is soluble in water so that the 1-aminoanthraquinone product is separated from the diluted mixture by filtration. The separated product is then washed with water until free of acid and then dried to provide the substantially pure 1-aminoanthraquinone product. The product may be recrystallized from glacial acetic acid if desired, but is directly obtained in sufficient purity for immediate use without further purification.

By the process of the present invention, the 1-aminoanthraquinone product is recovered in at least 70% yield and in a substantially pure state, e.g. above 90% purity. This product is suitable for further reaction without additional purification; thus, the 1-aminoanthraquinone obtained in this manner can be directly used as a valuable coupling agent or converted to other dyestuff intermediates, such as, 1-amino-4-bromoanthraquinone-2-sulfonic acid or 1-amino-2-bromo-4-hydroxyanthraquinone.

The 1-aminoanthraquinone-2-carboxylic acid starting materials of the present process are prepared by the general process of the following equation:

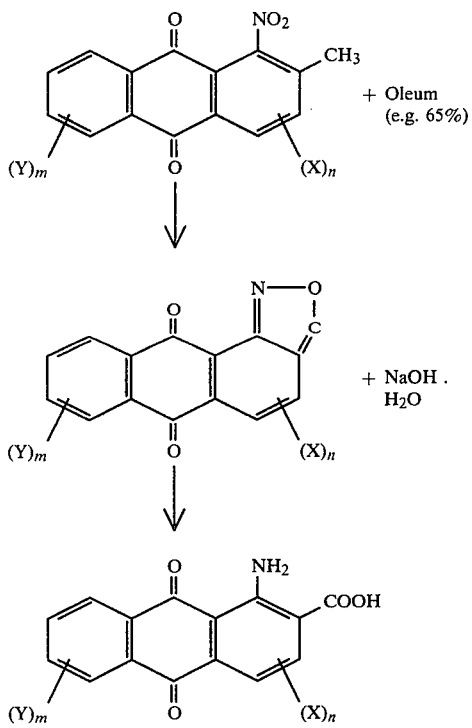

wherein X, Y, m and n are as defined above. This reaction, after the addition of oleum, is effected at a temperature between about −5° C. and about 10° C. under atmospheric pressure.

Having generally described the present invention, reference is now had to the accompanying examples which illustrate preferred embodiments, but which are not to be construed as limited to the scope of the present invention as set forth in the foregoing disclosure and in the appended claims. All amounts and proportions recited in the following examples are by weight unless otherwise indicated. It is also to be understood that any of the substituted 1-aminoanthraquinone-2-carboxylic acids can replace 1-aminoanthraquinone-2-carboxylic acid in the following examples to provide the corresponding, decarboxylated product.

EXAMPLE 1

1-Nitro-2-methylanthraquinone (30 g 0.11 mole) was added to 125 ml. of 65% oleum in portions sufficient to maintain the temperature below 5° C. The temperature at 5° C. is assisted by means of an ice-salt bath. After the addition was complete the mixture was stirred for 15 minutes at the same temperature. The reaction mixture was then poured slowly over ice. The dark brownish-yellow solid which formed was collected by filtration and washed with water. The wet cake was heated with 1130 ml. of 10% sodium hydroxide solution for one hour at 100° C. After being cooled to room temperature, the mixture was acidified with 6N hydrochloric acid. The solid 1-aminoanthraquinone-2-carboxylic acid which precipitated was collected by filtration and washed with water and dried.

To a three-necked round-bottomed flask equipped with stirrer and reflux condenser was added 2 g (0.007 mole) 1-aminoanthraquinone-2-carboxylic acid, 0.5 g (0.0018) zinc dust, 5 ml of 30% ammonium hydroxide solution and 30 ml of water. The resulting mixture was refluxed gently until evolution of carbon dioxide ceased, ca. 30 minutes. The mixture was then filtered while hot, and the filter cake was washed with water. The wet cake containing the zinc catalyst was heated over a steam bath with 50% sulfuric acid for one hour. Water was added and the solid product was collected by filtration and washed with water until acid-free. The product was dried to give 1.3 g (83.3% yield) of more than 90% pure 1-aminoanthraquinone.

EXAMPLE 2

Example 1 was repeated using 0.1 g (0.0018 Mole) of iron powder instead of zinc dust. A similar yield and product purity was obtained.

EXAMPLE 3

Example 1 was repeated using 1.9 g (0.007 mole) of 1-amino-4-hydroxyanthraquinone-2-carboxylic acid instead of 1-aminoanthraquinone-2-carboxylic acid. A good yield of substantially pure 1-amino-4-hydroxyanthraquinone was obtained.

EXAMPLE 4

Example 1 was repeated using 2.3 g (0.007 mole) of 1-amino-4-bromoanthraquinone-2carboxylic acid instead of 1-aminoanthraquinone-2-carboxylic acid. A good yield of substantially pure 1-amino-4-bromoanthraquinone was obtained.

What is claimed is:

1. A process for selectively producing a 1-amino anthraquinone which comprises:
   (a) forming a basic aqueous solution of ammonium hydroxide or an alkali metal hydroxide and an 1-aminoanthraquinone-2-carboxylic acid having the formula:

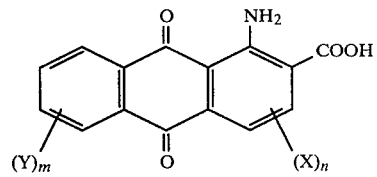

wherein X is hydroxy, alkoxy of from 1 to 4 carbon atoms, halo, amino or —SO₃H; Y is hydroxy, alkoxy of from 1 to 4 carbon atoms, halo, amino or —SO₃H; and m and n independently represent a value of from 0 to 2;

(b) contacting the resulting basic solution from (a) with between about 0.1 mole and about 0.5 moles of elemental zinc, tin or iron metal as the catalyst, per mole of 1-aminoanthraquinone-2-carboxylic acid at an elevated temperature to effect decarboxylation; and (c) recovering the corresponding product of the process having the formula:

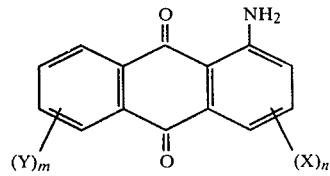

wherein the substituents X and Y and subscripts m and n are the same as defined above.

2. The process of claim 2 wherein the basic solution is an aqueous 0.1 to 5 molar solution.

3. The process of claim 2 wherein between about 2 and about 20 moles of the base per mole of the 1-aminoanthraquinone-2-carboxylic acid is employed.

4. The process of claim 1 wherein the decarboxylation is effected at between about 50° C. and about 150° C. under from about 5 psig to about 100 psig.

5. The process of claim 4 wherein the decarboxylation is effected at between about 80° C. and about 110° C. under atmospheric pressure.

6. The process of claim 1 wherein the 1aminoanthraquinone-2-carboxylic acid is unsubstituted as when m and n are 0.

7. The process of claim 1 wherein ammonium hydroxide is employed to form said basic solution.

8. The process of claim 1 wherein said metal is zinc.

9. The process of claim 1 wherein said metal is tin.

10. The process of claim 1 wherein said metal is iron.

* * * * *